United States Patent

Maes et al.

[11] Patent Number: 5,281,588
[45] Date of Patent: Jan. 25, 1994

[54] ORGANOMETALLIC COMPOUNDS, METHODS FOR THEIR PREPARATION AND PHARMACEUTICAL COMPOSITIONS CONTAINING THEM

[76] Inventors: Ludo Maes, Schillerstraat 40, 2050 Antwerpen; Emmanuel Bajyana-Songa, Rue Chasse à Prévost, 7504 Rumillies; Raymond Hamers, Vijversweg 15, 1640 Sint-Genesius-Rode, all of Belgium

[21] Appl. No.: 689,275
[22] PCT Filed: Dec. 13, 1989
[86] PCT No.: PCT/EP89/01541
§ 371 Date: Jul. 26, 1991
§ 102(e) Date: Jul. 26, 1991
[87] PCT Pub. No.: WO90/06931
PCT Pub. Date: Jun. 28, 1990

[30] Foreign Application Priority Data
Dec. 13, 1988 [FR] France ............... 88 16406

[51] Int. Cl.$^5$ ............ A61K 31/555; A61K 31/285; A61K 31/29; C07F 9/76
[52] U.S. Cl. .................. 514/184; 514/245; 514/503; 514/504; 544/181; 556/72
[58] Field of Search ........ 544/181; 514/245, 184, 514/503, 504; 556/72

[56] References Cited

U.S. PATENT DOCUMENTS
2,659,723  1/1947  Friedheim ............ 260/242
2,664,432 12/1953  Friedheim ............ 544/181

FOREIGN PATENT DOCUMENTS
0627057  9/1961  Canada ................ 544/181
1229543  6/1967  Fed. Rep. of Germany.
655435   7/1951  United Kingdom.

*Primary Examiner*—John M. Ford
*Assistant Examiner*—Y. N. Gupta
*Attorney, Agent, or Firm*—Keck, Mahin & Cate

[57] ABSTRACT

A method for treating trypanosomiases, leishmanioses, filariases and pneumonias caused by Pneumocystis carinii, comprising the step of administering an effective amount of an organometallic compound of the formula:

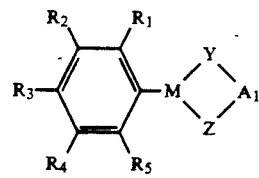

in which:
M is arsenic or antimony,
Y and Z are identical or different and are each sulfur or oxygen,
$R_1$, $R_2$, $R_3$, $R_4$ and $R_5$ are identical or different and are each hydrogen or a group of the formula:

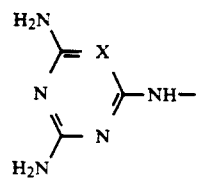

in which
X is nitrogen, and
$A_1$ is an alkylene group of 3 to 21 carbon atoms, that is unsubstituted or substituted by: one or more groups which are identical or different and which are of the formula: $-(CH_2)_n-R_7$ in which $R_7$ is $-H$, $-OH$, $-COOH$, $-NH_2$ or $-SO_3H$ and n is an integer of 0 to 10; or one or more Na or K salts of said one or more groups of the formula: $-(CH_2)_n-R_7$, when $R_7$ is $-COOH$; or one or more hydrochlorides of said one or more groups of the formula: $-(CH_2)_n-R_7$ when $R_7$ is $-NH_2$; at least one of said $R_1$, $R_2$, $R_3$, $R_4$ or $R_5$ not being hydrogen; with the exception of the compound of formula (I):

(Abstract continued on next page.)

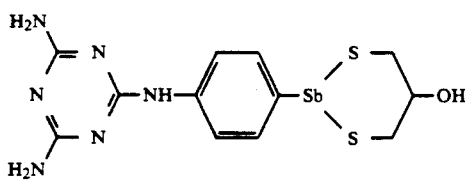
and a pharmaceutically acceptable vehicle.
5 Claims, No Drawings

ORGANOMETALLIC COMPOUNDS, METHODS FOR THEIR PREPARATION AND PHARMACEUTICAL COMPOSITIONS CONTAINING THEM

The present invention relates to organometallic compounds, methods for their preparation as well as pharmaceutical compositions containing the said compounds. The subject of the invention is more particularly the use of such pharmaceutical compositions in the treatment of parasitic diseases such as the trypanosomiases and the filariases.

The chemotherapeutic treatment of these parasitic diseases in man and animals poses serious problems at the present time.

The compound Mel B, discovered by E. FRIEDHEIM (patent filed in the UNITED STATES and published in 1953 under the U.S. Pat. No. 2,659,723) is the most commonly used medicine for the treatment of second stage human trypanosomiases. However, this compound possesses many disadvantages, one of the most serious of which is the triggering of unpredictable lethal encephalopathies which are produced in 5% of the individuals treated with Mel B (WHO/FAO EXPERT COMMITTEE (1979); The African Trypanosomiases. WHO TECHNICAL REPORT SERIES, N 635).

This patent also describes other compounds related to Mel B possessing an atom of arsenic (As) or antimony (Sb) forming part of a 5-membered ring structure. A process likely to lead to the production of a derivative related to Mel B in which an atom of antimony forms parts of a 6-membered ring structure is described as an example in this patent.

However, no physicochemical or biological property of the product likely to be obtained in the above-mentioned example (which corresponds to 2-p-(4,6-diamino-s-triazin-2-yl-amino) phenyl-1,3,2-dithia stibane-4,5,6-triol) was mentioned in this patent.

The compound Mel W (FRIEDHEIM E. A. H. (1966) German patent No. 1,229,543) is a water-soluble derivative of Mel B, and has been used in veterinary and human therapy. However, this latter application has been abandoned on account of many problems of toxicity.

In addition to the problem of the toxic effect of the medicines mentioned above, a considerable number of strains of trypanosomes resistant to these products has also been discovered.

These two medicines, Mel B and Mel W, are compounds similar to the dithiarsolane type with 5 members (5-membered ring); the only structural difference between these two compounds consists of a different substituent on the 5-membered ring. The synthesis of this 5-membered ring is carried out starting from vicinal dithiols (i.e. thiols borne by two neighbouring carbon atoms).

The present invention relates to the organometallic compounds represented by the following general formula:

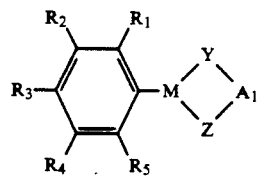

in which:
M represents arsenic (As) or antimony (Sb),
Y and Z, identical or different, represent a sulfur or oxygen atom,
$R_1$, $R_2$, $R_3$, $R_4$ and $R_5$, identical or different, represent:
  a hydrogen atom,
  a primary amine-$NH_2$, or a secondary amine or a tertiary amine, substituted by one or two alkyl groups of 1 to 18 carbon atoms, a group of formula

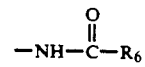

in which $R_6$ represents a methyl —$CH_3$ or an amine —$NH_2$,
  a group

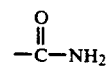

a —$NO_2$ group
  a —COOH group
  a —OH group
  a group of the type

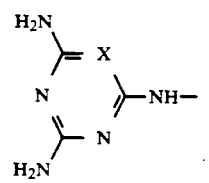

in which
X represents a nitrogen atom or a CH group,
$A_1$ represents an alkylene group of 3 to 21 carbon atoms, and in particular from 4 to 6 carbon atoms, this alkylene group being substituted, where appropriate:
  either by a group of formula: —$(CH_2)_n$—$R_7$ in which $R_7$ represents a hydrogen atom, or a hydroxyl —OH, or an acid —COOH, or an amine —$NH_2$, or a sulfonic —$SO_3H$ function, and n represents an integer varying from 0 to 10, or by several identical or different groups of formula —$(CH_2)_n$—$R_7$ mentioned above,
  or by one or more salts of the group of formula —$(CH_2)_n$—$R_7$ defined above, in particular one or more salts of Na or K when $R_7$ represents an acidic function or one or more hydrochlorides when $R_7$ represents an amine function,
with the exception of the compound of formula (I):

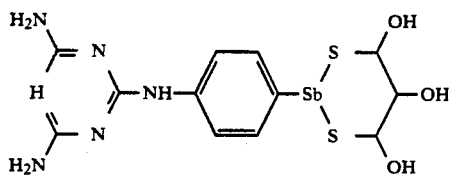

designated hereafter by:
2-p-(4,6-diamino-s-triazin-2-yl-amino)phenyl-1,3,2-dithia-stibane-4,5,6-triol.

The present invention relates more particularly to the compounds represented by the following general formula:

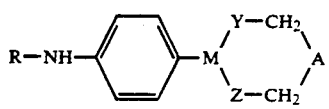

in which:
M represents arsenic (As) or antimony (Sb),
Y and Z, identical or different, represent a sulfur or oxygen atom,
R represents a hydrogen atom or a group of the following formula:

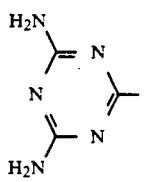

A represent an alkylene group of 1 to 18 carbon atoms, in particular from 2 to 4 carbon atoms, possibly substituted by one or more hydroxyl —OH functions.

The subject of the invention is more particularly the following compounds:

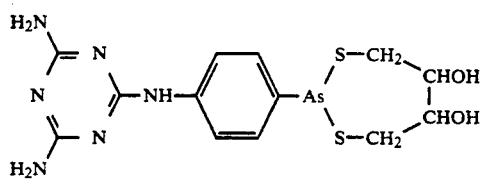

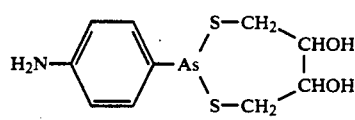

The present invention also relates to the process for obtaining the compounds defined above, comprising the reaction between
the compound of formula

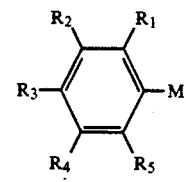

in which $R_1$, $R_2$, $R_3$, $R_4$ and $R_5$ have the meanings indicated above, and M represents an oxide, or acid or acid salt form or the dichloride of arsenic (As) or antimony (Sb), on the one hand,
and on the other, the compound of formula:

in which Y, $A_1$ and Z have the meanings indicated above, followed by the recovery and purification of the compounds obtained.

The subject of the present invention is more particularly the process for obtaining the specific compounds defined above, comprising the reaction between
on the one hand, the compound of formula

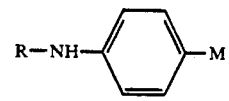

in which
R has the meaning indicated above and M represents an oxide or acid or acid salt form or the dichloride of arsenic (As) or antimony (Sb),
and on the other, the compound of formula

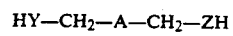

in which Y, Z and A have the meanings indicated above, followed by the recovery and purification of these compounds.

Conditions under which the starting compounds for the above-mentioned reaction are obtained and used are wellknown to the person skilled in the art and appear in particular in the detailed description which follows of the synthesis of the derivatives of the invention.

The invention also relates to the use of the compounds defined above, including the derivative of formula (I) mentioned above, to obtain medicines designed for the treatment of trypanosomiases, leishmaniases, diseases caused by filaria (filariases) and infections due to Pneumocystis carinii, in particular in individuals suffering from AIDS.

The subject of the invention is pharmaceutical compositions containing one or more trypanocidal compounds defined above, including the derivative of formula (I) mentioned above, in combination with a pharmaceutically acceptable vehicle.

These pharmaceutical compositions are particularly efficacious for the treatment of parasitic diseases such as those caused by the trypanosomes, in particular sleeping sickness, and by the filaria; these compositions also seem particularly efficacious for the treatment of other diseases such as the pneumonias caused by Pneumocystis carinii.

Advantageously, the compounds of the invention are combined with a pharmaceutically acceptable vehicle in the form of a suspension in a physiological liquid for intramuscular or subcutaneous administration. Such compositions are particularly useful compared with the trypanocidal medicines currently used such as Mel B, since this latter is administered in an organic solvent which is an irritant causing painful inflammations which limit its use.

The pharmaceutical compositions of the invention can be used for the purpose of preventing or treating the above-mentioned parasitic diseases in man or animals (veterinary use).

It has also been observed that these compositions are active against the strains of trypanosomes resistant to melarsoprol (Mel B).

According to the results obtained in studies carried out on mice, the compounds of the invention are much less toxic than the trypanocidal derivatives based on arsenic or antimony in current use.

The good stability as well as the low solubility of the compounds of the invention in physiological fluids make them compounds of choice for use in slow-release pharmaceutical compositions which consequently, have a prolonged time of action.

The invention is more particularly illustrated with the aid of the examples which follow:

EXAMPLE 1

Synthesis of the following compound:

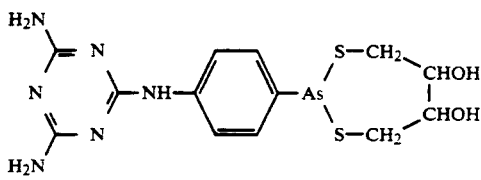

The synthesis is carried out starting from 4,6-diamino 2-chloro-s-triazine which is condensed with p-arsanilic acid (Banks) by refluxing.

The product thus obtained, the 2-(p-arsonoanilino)- 4,6-diamino-2-triazine of formula:

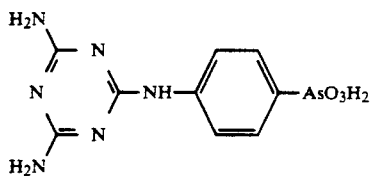

is reduced by means of sulfur dioxide to give the p-(4,6- diamino-s-triazin-2-yl-amino)-phenylarsenone dihydrate (II) of formula:

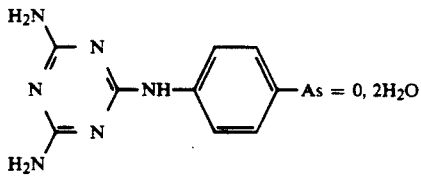

Then 246 mg (0.75 mmole) of this intermediate product (II) are dissolved in 10 ml of methanol. The solution is stirred vigorously under nitrogen at room temperature. Then 127 mg (0.825 mmole) of 1,4-dimercapto 2,3- butanediol of formula HS—CH$_2$—CHOH— CHOH—CH$_2$—SH (JANSSEN) dissolved in 5 ml of methanol are added slowly, the reaction mixture being maintained under an atmosphere of nitrogen. A white precipitate is formed and stirring is continued for 1 hour. The suspension is filtered through a glass filter. After being washed, the white solid obtained is dried in a desiccator in a vacuum. The reaction yield is about 98%. The compound obtained is 2-p-(4,6-diamino-s-triazin-2-yl-amino) phenyl 1,3,2-dithiarsepane-5,6-diol; M.p.=220° C.

The last step of this synthesis may also be carried out in aqueous medium.

In mice infected with Trypanosoma evansi (or T. evansi), the trypanosomes of the blood are eliminated in 24 hours with a dose of 5 mg/kg of the derivative of the invention described above given by subcutaneous injection or with a dose of 2.5 mg/kg following intramuscular injection.

In the case of the infection of mice with T. gambiense, the trypanosomes of the blood are eliminated in 48 hours with a dose of 5 mg/kg of the above-mentioned derivative of the invention by subcutaneous or intramuscular injection.

The parasitemia obtained by infection of mice with a strain of T. rhodesiense resistant to melarsoprol disappeared after three days by using an intramuscular dose of 10 mg/kg. With a single dose of 5 mg/kg by the intramuscular route, a prophylaxis of about 12 days is obtained against T. evansi. The medicine is well tolerated; the treated mice do not show any local reaction or any clinical sign of toxicity in the central nervous system after subcutaneous injection of up to 500 mg/kg.

EXAMPLE 2a

Synthesis of the following compound:

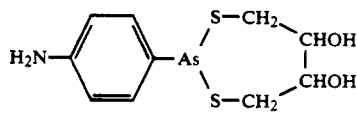

219 mg (1 mmole) of p-aminophenylarsenone dihydrate of formula

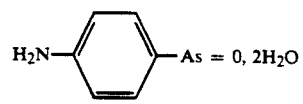

obtained by reduction of p-arsanilic acid with the aid of sulfur dioxide according to methods known to the person skilled in the art, are dissolved in 8 ml of methanol. The solution is placed under nitrogen. 170 mg (1.1 mmole) of 1,4-dimercapto 2,3-butanediol dissolved in 2 ml of methanol are then added slowly while the solution is well stirred. An opal coloured viscous material precipitates on the walls of the reaction vessel. Stirring is continued for 3 hours; in the meantime, the product has been transformed and has the appearance of a white solid precipitate.

The reaction mixture is filtered and the product recovered is washed with methanol and dried.

The product obtained, which is in the form of easily powdered white flakes, is 2-p-aminophenyl 1,3,2- dithiarsepane-5,6-diol.

It is insoluble in methanol and ethanol; it is soluble in concentrated hydrochloric acid and in boiling acetic acid.

EXAMPLE 2b

Synthesis of the compound described in example 2a:
0.5 mmole of sodium arsanilate of formula:

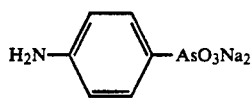

are dissolved in 10 ml of water. The solution is placed under nitrogen; a solution of 1.5 mmole of 1,4-dimercapto 2,3-butanediol in 5 ml of water is added with vigorous stirring. The stirring of the reaction mixture is continued for 3 hours, then the product is recovered and purified.

EXAMPLE 3

Synthesis of the following compound:

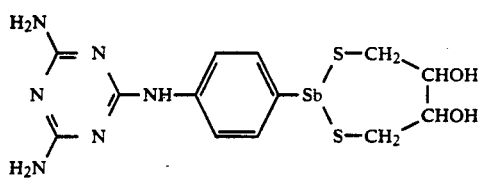

0.1 mmole of:

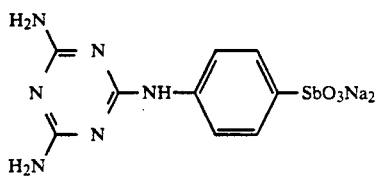

are dissolved in 10 ml of water. 0.5 mmole of 1,4-dimercapto 2,3-butanediol are added with stirring and under an atmosphere of nitrogen. After a reaction time of 1 hour, the product is recovered and purified.

EXAMPLES 4 TO 8

The compounds of the type:

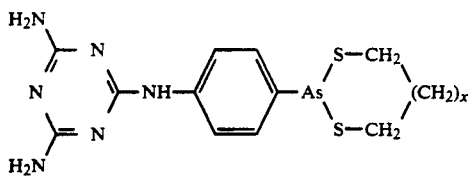

for which x=1,2,3,4 and 6 are obtained, respectively, by following the same method as that described in example 1, starting from p-(4,6-diamino-s-triazin-2-yl-amino)-phenylarsenone of formula

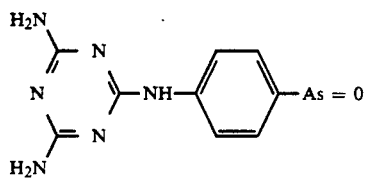

and 1,3-dimercapto-propane, HS—(CH$_2$)$_3$—SH (Janssen Chimica) 1,4-dimercapto-butane, HS—(CH$_2$)$_4$—SH, 1,5-dimercapto-pentane, HS—(CH$_2$)$_5$—SH, 1,6-dimercapto-hexane, HS—(CH$_2$)$_6$—SH, and 1,8-dimercapto-octane, HS—(CH$_2$)$_8$—SH (Aldrich).

We claim:

1. A method for treating trypanosomiases, leishmanioses, filariases and pneumonias caused by Pneumocystis carinii, comprising the step of administering an effective amount of an organometallic compound of the formula:

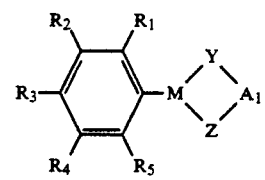

in which:

M is arsenic or antimony,

Y and Z are identical or different and are each sulfur or oxygen, $R_1$, $R_2$, $R_3$, $R_4$ and $R_5$ are identical or different and are each hydrogen or a group of the formula:

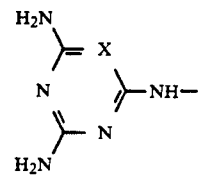

in which

X is nitrogen, and $A_1$ is an alkylene group of 3 to 21 carbon atoms, that is unsubstituted or substituted by: one or more groups which are identical or different and which are of the formula: —(CH$_2$)$_n$—R$_7$ in which R$_7$ is —H, —OH, —COOH, —NH$_2$ or —SO$_3$H and n is an integer of 0 to 10; or one or more Na or K salts of said one or more groups of the formula: —(CH$_2$)$_n$—R$_7$, when R$_7$ is —COOH; or one or more hydrochlorides of said one or more groups of the formula: —(CH$_2$)$_n$—R$_7$ when R$_7$ is —NH$_2$: at least one of said $R_1$, $R_2$, $R_3$, $R_4$ or $R_5$ not being hydrogen; with the exception of the compound of formula (I):

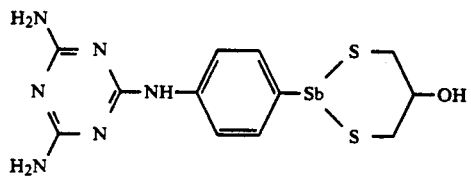

and a pharmaceutically acceptable vehicle.

2. A method of claim 1, wherein $A_1$ is an alkylene group of 4 to 6 carbon atoms.

3. A method of claim 1, wherein $R_1$, $R_2$, $R_4$ and $R_5$ are hydrogen, X is nitrogen, and $A_1$ is an alkylene group of 3 to 20 carbon atoms that is unsubstituted or substituted by one or more groups: —(CH$_2$)$_n$—R$_7$ in which R$_7$ is —OH.

4. A method of claim 3, wherein $A_1$ is an alkylene group of 4 to 6 carbon atoms.

5. A method of claim 4, wherein the organometallic compound is of the formula:
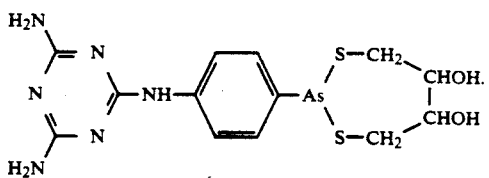
* * * * *